United States Patent [19]

Hawk

[11] Patent Number: 4,727,872
[45] Date of Patent: Mar. 1, 1988

[54] ENDOTRACHEAL INTUBATION SYSTEM

[76] Inventor: Pablo Hawk, Ferrocarril Viejo No. 31, Coyoacan 21, D.F., Mexico, 04000

[21] Appl. No.: 920,776

[22] Filed: Oct. 20, 1986

[51] Int. Cl.⁴ .............................................. A61M 16/00
[52] U.S. Cl. ........................... 128/207.14; 128/207.15; 604/43
[58] Field of Search ...................... 128/200.26, 207.14, 128/207.15, 202.13, 200.24, DIG. 26, 3, 4, 10, 20; 604/174, 43; 269/68, 45, 328

[56] References Cited

U.S. PATENT DOCUMENTS

| | | | |
|---|---|---|---|
| 1,645,023 | 10/1927 | Richards | 269/68 |
| 3,464,411 | 9/1969 | Martinez | 128/200.24 |
| 4,049,000 | 9/1977 | Williams | 128/20 |
| 4,230,108 | 10/1980 | Young | 128/207.15 |
| 4,424,724 | 1/1984 | Bookwalter et al. | 128/20 |
| 4,562,832 | 1/1986 | Wilder et al. | 128/20 |
| 4,573,452 | 3/1986 | Greenberg | 128/20 |
| 4,637,389 | 1/1987 | Heyden | 604/43 |

FOREIGN PATENT DOCUMENTS 2522972  9/1983  France ............................ 128/204.25

*Primary Examiner*—Edward M. Coven
*Attorney, Agent, or Firm*—H. Mathews Garland

[57] ABSTRACT

An endotracheal intubation system including straight and curved cannulas, and cannula support apparatus comprising a bridge connectable over a patient table, and an adjustable mounting block assembly for supporting a cannula over the table in position in the mouth and throat of a patient.

8 Claims, 10 Drawing Figures

ENDOTRACHEAL INTUBATION SYSTEM

BACKGROUND OF THE INVENTION

1. Field of the Invention

This invention relates to a medical apparatus and systems and more particularly to introducing and supporting a plurality of tubes extending in side-by-side relation into a patient through the patient's mouth, when the patient is unconscious as during surgery, or during other procedures referred to as endotracheal intubation.

2. History of the Prior Art

While carrying out both surgical and examination procedures on a patient, it is often necessary to introduce a variety of tubes simultanously through the mouth and throat of the patient. At the same time that anesthesia is being administered to the patient, such procedures as microlaryngeal surgery and examination procedures such microlaryngoscopy may be performed on a patient. To simultaneously give anesthesia and perform an examination or surgery through the throat of a patient, it is desirable to have means for separately supporting tubes in parallel relationship extending into the patient's mouth and downwardly through the pharynx, the upper part of the esophagus, the larynx, and the trachea. It is desirable that such tubes extend through separate defined passageways so that one may be easily inserted or removed without disturbing the other. Such procedures involve the use of either a straight or a curved cannula, depending upon the particular procedures performed. A straight cannula may be used for cases under direct vision like microlaryngeal surgery. A curved cannula may be used with fibre optic light devices as in microlaryngoscopy. Both straight and curved cannula provide the opportunity to achieve endotracheal intubation with the fibre optic aid of the bronchoscope with a light.

A number of devices are known for supporting and guiding one or more tubes through the throat of a patient for a variety of purposes. Examples of various types of such devices are shown in the following U.S. patents: U.S. Pat. No. 1,498,810 issued June 24, 1924 to J. G. Poe; U.S. Pat. No. 2,127,215 issued Aug. 16, 1938 to J. T. Gwathmey; U.S. Pat. No. 2,599,521 issued June 3, 1952 to R. A. Berman; U.S. Pat. No. 2,705,959 issued Apr. 12, 1955 to Cal Elmore U.S. Pat. No. 3,756,244 issued Sept. 4, 1973 to John M. Kinnear, et al; U.S. Pat. No. 3,908,665 issued Sept. 30, 1975 to John A. Moses; U.S. Pat. No. 4,198,970 issued Apr. 22, 1980 to Raymond Luomanen; U.S. Pat. No. 4,256,099 issued Mar. 17, 1981 to Gale E. Dryden; and U.S. Pat. No. 4,363,320 issued Dec. 14, 1982 to Michael Cossove. While these patents show a variety of cannula designs, none of them show or suggest the specific designs of the present invention and methods and apparatus for adjustably and securely supporting the devices while they are being used for both surgery and examination. Such apparatus as face plates has been used to hold a cannula in place.

SUMMARY OF THE INVENTION

In accordance with the invention, there is provided an endotracheal cannula and a system for supporting the cannula during intubation of a patient. One form of cannula comprises a curved portion joined with an integral straight portion. Another form is straight. Both cannulas are provided with side-by-side passageways for tubes. One side of the cannula housing around one of the passage openings is shorter than the other side at the straight end portion end of the curved form. One end of the straight form is tapered. The system for supporting the cannula includes a bridge assembly spanning an operating table supporting the cannula above a patient from an adjustable mounting assembly permitting the cannula to be aligned at a plurality of angles relative to the vertical for a variety of surgical and examination procedures.

It is a principal object of the invention to provide a new and improved endotracheal cannulas.

It is an other object of the invention to provide a system for supporting an endotracheal cannula above a patient on an operating table.

It is another object of the invention to provide an supporting structures for an endotracheal cannula above a patient on an operating table by angular and lateral movement to facilitate introduction of an endotracheal cannula into a patient's throat.

The above and other objects and features of the invention will be apparent to those skilled in the art from the following detailed description of the invention taken in conjunction with the accompanying drawings in which preferred embodiments of the devices of the invention are shown.

DESCRIPTION OF THE PREFERRED EMBODIMENT

Figure 2A:
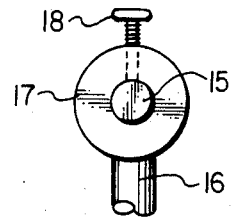
FIG. 2A is a side view along line 2A—2A of FIG. 2.
Figure 1:
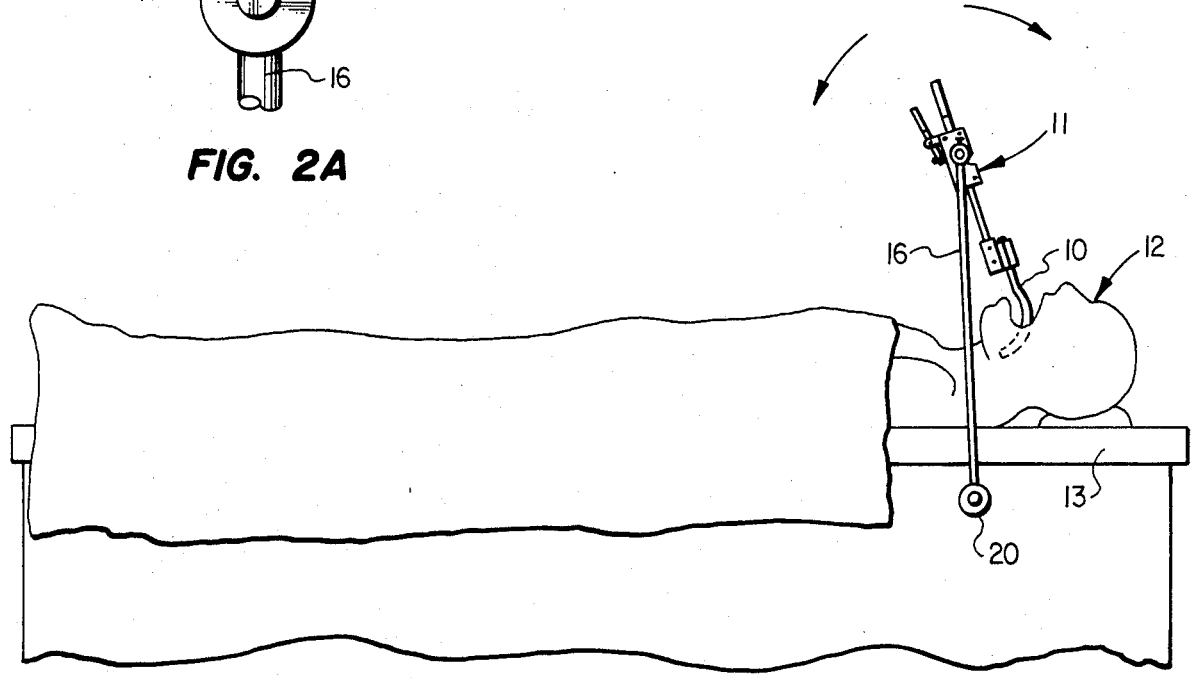
FIG. 1 is a side view in elevation of a patient on an operating or examination table showing an endotracheal cannula supported in the mouth and throat of the patient by a system including the features of the invention.
Figure 2:
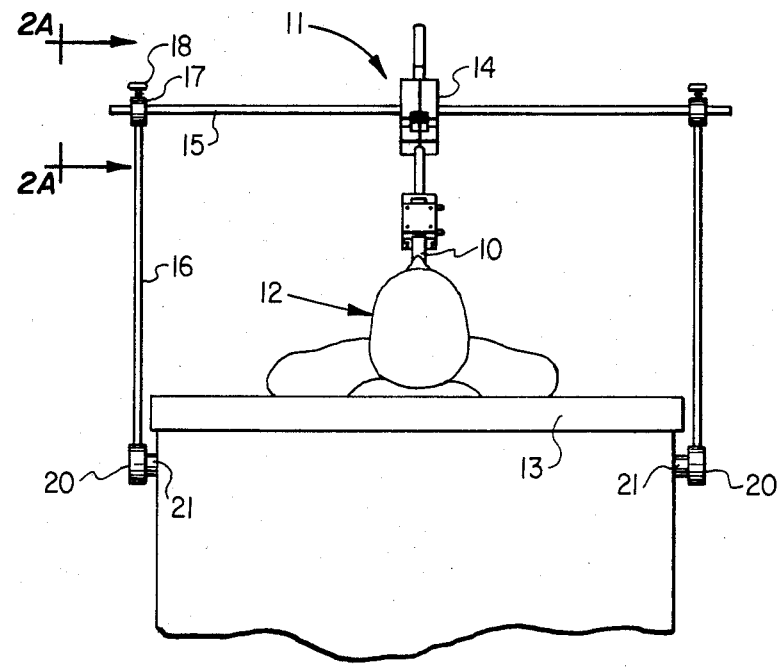
FIG. 2 is a head end view in elevation of the patient and apparatus of the invention as shown in FIG. 1.
Figure 3:
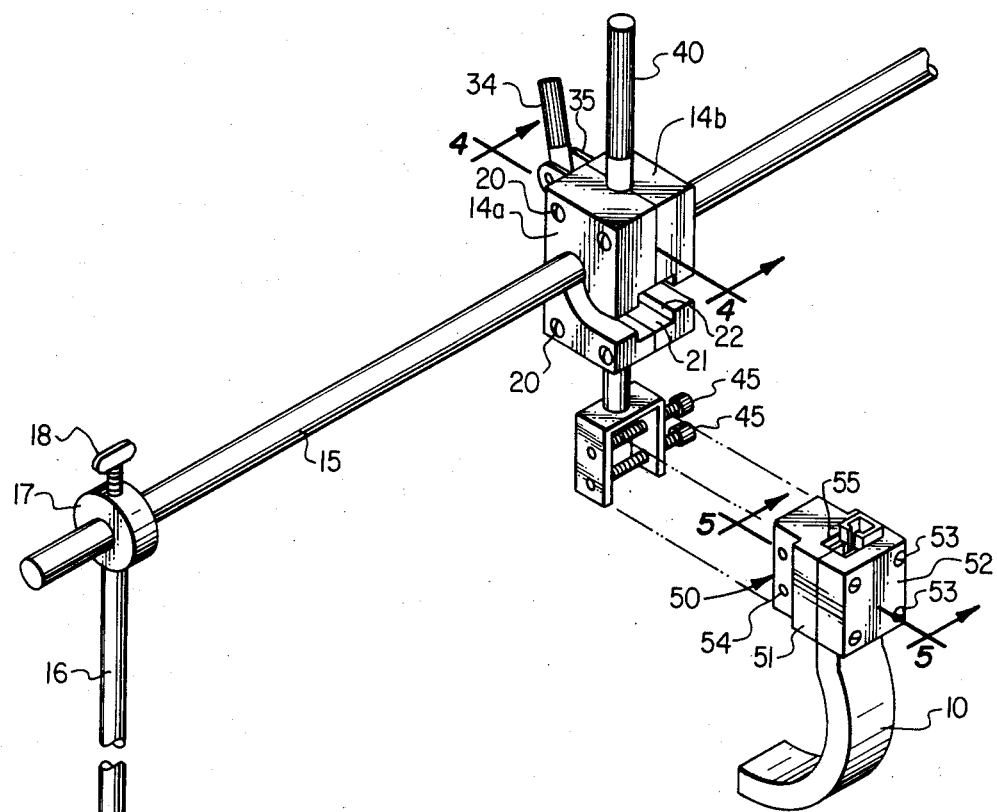
FIG. 3 is a fragmentary exploded view in perspective of the devices of the invention including the curved endotracheal cannula and the support system.
Figure 4:
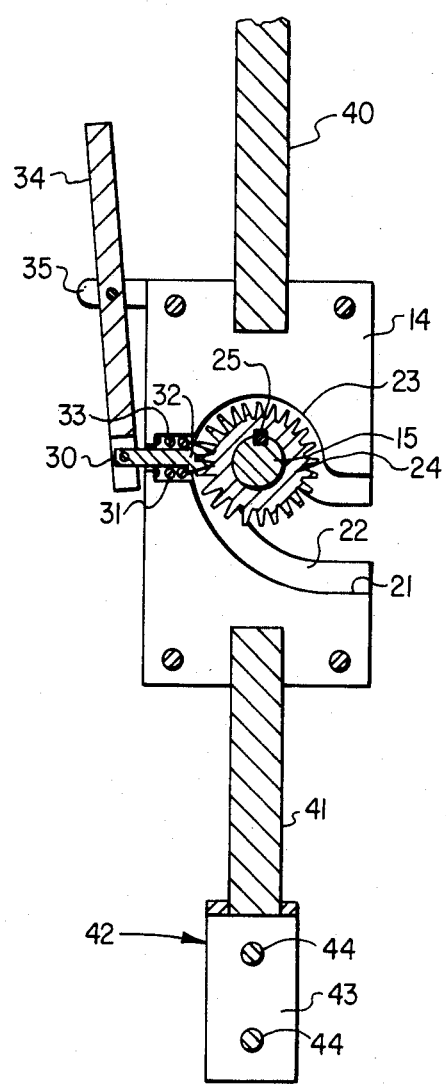
FIG. 4 is an enlarged side view in section of the adjustable features of the support for the cannula.
Figure 5:
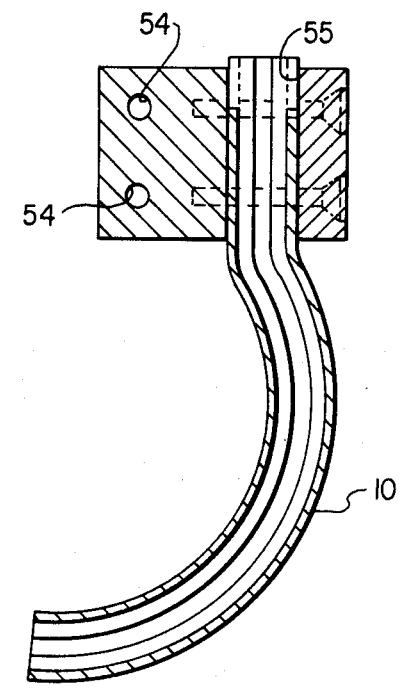
FIG. 5 is an enlarged side view in section of the cannula and mounting block for the cannula as seen in FIG. 3.

Referring to FIG. 1, a curved endotracheal cannula 10 is illustrated suspended from a support system 11 in the mouth and throat of a patient 12 resting on an operating or examination table 13. As shown in FIGS. 1 and 2 the support system 11 includes a mounting body 14 adjustably secured on an inverted U-shaped bridge formed by a horozontal bar 15 and legs 16 having end mounting sleeves 20 secured on pins 21 permitting angular adjustment of the bridge over the patient. The bar 15 is mounted in sleeves 17 on legs 16. Screws 18 in sleeves 17 secure the bar in the sleeves and allow the bar to be adjusted horizontally. Referring to FIGS. 3-5, the body 14 is formed by two longitudinal halves 14a and 14b held together by screws 20 threaded through the body member 14a into the body member 14b. The body 14 has a front opening slot 21 having an enlarged central portion defined between opposite side edges 22. The slot 21 extends into the body curving upwardly generally along the vertical axis of the body terminating in a cylindrical transverse slot portion 23. As seen in FIGS. 3 and 4, the slot 21 opens through the opposite side faces of the body halves 14a and 14b. The configuration of the slot 21 is designed particularly to permit the body 14 to be installed on the bar 15 for pivotal movement thereon. The body 14 is mounted on the bridge on a tubular shaped gear 24 locked on the central portion of the bar 15 by a key 25. The key 25 fits into corresponding keyways within the gear and along the central portion of the bridge. The diameter of the gear 24 is slightly less than the diameter of the slot portion 23 to permit the body 14 to freely rotate on the gear. The length of the gear is less than the transverse distance across the body between the slot internal side faces 22. The design of the gear and the internal slot 21 in the body 14 permits the body to freely rotate on the bar 15 while being locked at a near central position on the bridge as shown. The design of the bridge, gear, and body 14 can be such as to allow axial or lateral movement of the body on the horizontal part of the bridge to facilitate alignment between patient and cannula. For example, the key 25 and key slots in the bar 15 may be lengthened to allow the gear and body 14 to slide along the bar for lateral adjustment across the table to the patient position. An indexing locking latch 30 is mounted in a bore 31 extending from the body back face intersecting the cylindrical portion 23 of the slot 21. The indexing latch has an inward enlarged forked head 32 configured to engage the teeth on the gear 24 for releaseably locking the body 14 at different angular positions on the bridge 15. A coil spring 33 around the indexing latch within the bore 31 urges the indexing latch inwardly into meshing, locking relationship with the teeth on the gear 24. The outward end portion of the indexing latch is pinned to an operating handle 34 for retracting the indexing latch to release the latch from the gear. The handle 34 is pinned between side brackets 35 connected on the back face of the upper end of the body 14 so that the handle 34 may pivot on the brackets 35 to engage and disengage the indexing latch 30. An operating handle 40 is secured into the top of the body 14 for changing the angular position of the body on the bridge when the latch is disengaged. As viewed in FIG. 4, the indexing latch handle 34 may be moved clockwise to disengage the indexing latch 30 from the gear 24 releasing the body 14 so that the operator may grasp the handle 40 on the body to change the angular position of the body 14 on the bridge. When the desired position is reached the indexing handle 34 is released allowing the spring 33 to move the indexing latch inwardly reengaging the gear and locking the body 14 on the bridge. A rod 41 is secured at an upper end into the bottom of the body 14. A downwardly opening U-shaped bracket 42 having downwardly extending opposite side legs 43 is secured on the lower end of the rod 41. The two bracket legs 43 are each provided with a pair of vertically spaced holes 44 aligned horizontally with each other to receive mounting pins 45 for connecting a cannula mounting block 50 in the bracket. As seen in FIG. 3, the cannula mounting block 50 is formed by a T-shaped back member 51 and a front plate 52 secured by screws 53 to the back member. Some lateral movement of the block 50 along the pins 45 may be provided for further horizontal adjustment of the cannula 10. The reduced portion of the back member 51 has horizontal holes 54 for the pins 45 so that the mounting block is secured with the bracket 42 by the pins 45 extending through the bracket legs 43 and horizontal holes 54 in the reduced portion of the back member. The inside contacting surfaces of the mounting block members 51 and 52 are configured to provide a vertical slot 55 in the mounting block through which the straight upper end portion of the cannula 10 fits. The straight portion of the cannula as seen in FIG. 5 is clamped in the mounting block when the two portions of the mounting are screwed together as illustrated.

Figure 6:
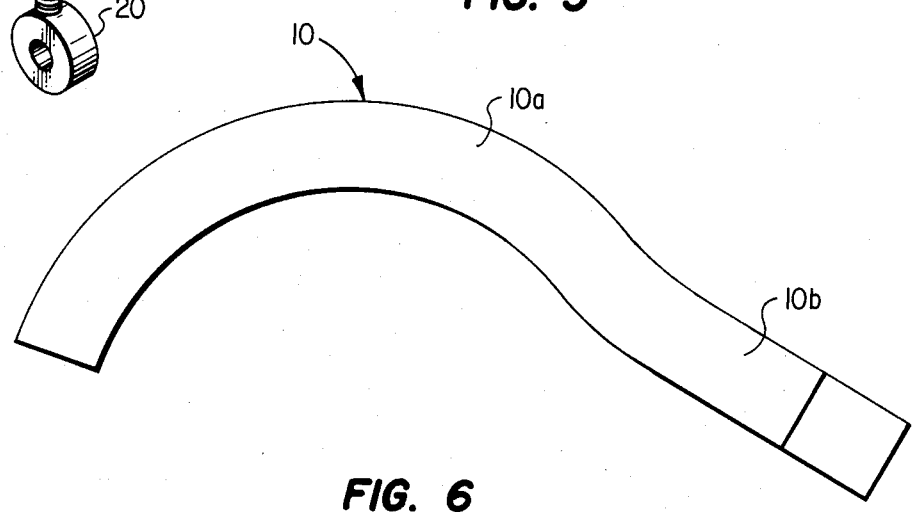
FIG. 6 is a side view in elevation of the curved cannula shown in FIG. 5.
Figure 7:
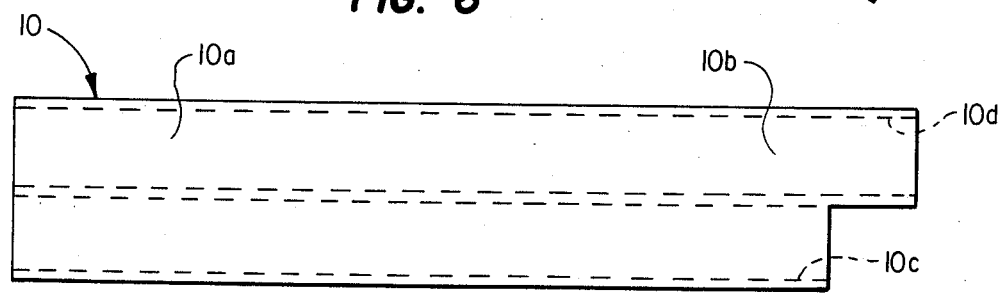
FIG. 7 is a top view of the cannula as shown in FIG. 6.
Figure 8:
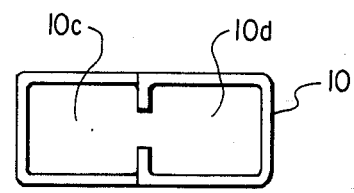
FIG. 8 is a right end view of the cannula in FIGS. 6 and 7.
Figure 9:
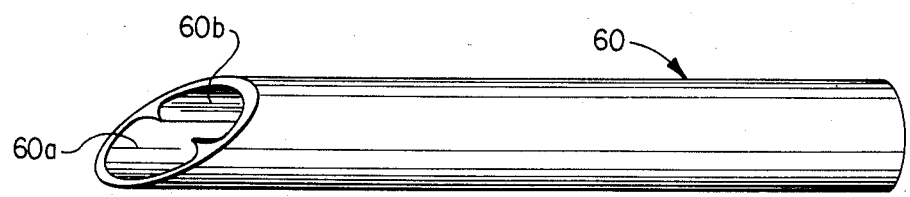
FIG. 9 is a side view in elevation of a straight cannula in accordance with the invention.

In accordance with the invention, two forms of endotracheal cannulas may be used for operating on and examining a patient. Both of curved cannula 10 shown in FIGS. 1–3, 7, and 6–8 and the straight cannula shown in FIG. 9 may be supported by the system 11, depending upon the particular surgical operation or examination to be performed. Referring to FIGS. 6–8, the curved cannula 10 has a curved portion 10a and an integral straight portion 10b. As evident in FIGS. 7 and 8, the cannula is provided with parallel side-by-side passageways 10c and 10d extending throughout the length of the cannula to accommodate two tubes, surgical instruments, and the like. As illustrated in FIGS. 6 and 7, the straight end 10d of the cannula has one side shortened so that the passage 10c is not as long as the passage 10d, opening in the straight end inwardly from the opening of the passage 10d. The curved portion of the cannula fits through the mouth into the throat of the patient as evident in FIG. 1, while the straight portion is clamped in the support block 50 for supporting the cannula in place in the patient from the system 11. A straight form of cannula 60 is illustrated in FIG. 9. The cannula 60 has parallel side by side passages 60a and 60b extending throughout the length of the cannula. As shown, one end of the cannula is tapered so that the passage 60b at such end is shorter than the passage 60a. The provisions of the shorter passage in both the cannula 10 and the straight cannula 60 facilitates the extraction of the cannula while leaving in place an endotracheal tube. Both cannulas are preferrably made of plastic so that they are less expensive, disposable, and less traumatic for a patient.

The curved cannula 10 or the straight cannula 60 is used to perform such operative procedure or examination upon a patient as is desired or necessary. The straight end portion of the curved cannula or the tapered end of the straight cannula is clamped in the mounting block 50 which is then secured by the pins 45 in the bracket 42. The body 14 may already be on the bar 15 or may now be installed on the bar. The body is mounted on the bar by manipulating the body over the bar along a path to guide the bar and the gear 24 into the slot 21 to the position illustrated in FIG. 4. When placing the body on the bar, the indexing latch 30 should be retracted with the handle 34. With the patient in position below the bridge, the cannula 10 is inserted into the mouth and throat of the patient to the desired position. The handle 34 is then released allowing the spring 33 to press the latch 30 inwardly until the head of the latch engages the teeth on the gear 24 to lock the body 14 with the cannula 10 at the desired operating position. The necessary tubes and/or instruments then may be inserted into the patient through the cannula 10. The straight cannula 60 is installed using the same procedural steps. The angular and lateral adjustablity of both the body 14 on the bar 15 and of the bar on the operating or examination table permits maximum flexibility of the positioning of the cannula with respect to the patient.

The many different applications of the cannula and the support system will be evident. For example, the straight cannula can be used advantageously for removal of laringeal tumors with microscopical help using long alligator forceps. The curved cannula can be used for the removal laringeal tumors through indirect vision using a fibreoptic broncoscope. Both of the cannulas permit the introduction of a naso-gastric tube in cases of abdominal surgery. The mounting system permits both vertical and horizontal adjustment. The angular adjustment features allows for positioning the cannulas to obtain an optimum field in microlaryngoscopy.

What is claimed is:

1. An endotracheal intubation system comprising:
   an endotracheal cannula;
   bridge means connectable with a patient table over a patient on said table;
   means connected with said cannula for adjustably supporting said cannula on said bridge means suspended in the mouth and the throat of a patient on said table, said supporting means comprising a mounting block connected with said cannula, a mounting body connected with said mounting block, and means coupling said mounting body on said bridge means for selectively positioning said body with said cannula and mounting block at desired angular positions on said bridge means; and
   said means for coupling said mounting body on said bridge means comprises an annular indexing gear having circumferentially spaced peripheral teeth on said bridge means, means defining a slot in said mounting body sized to receive an indexing latch member and an indexing latch finger pivotally secured in said body for releasable engagement with said teeth of said indexing gear permitting said mounting body to be positioned and locked at a plurality of angles on said bridge means.

2. An endotracheal intubation system in accordance with claim 1 wherein said cannula has a straight first end portion disposed through said mounting block and a curved second end portion contoured to fit a patient's mouth and throat and provided internally with a plurality of separate parallel passageways extending throughout the length of said cannula.

3. An endotracheal intubation system in accordance with claim 2 wherein one of said passages through said cannula terminates in said straight end portion of said cannula at a location spaced inwardly from the termination of the other of said passages.

4. An endotracheal intubation system in accordance with claim 1 wherein said cannula is a tubular straight member having plurality of parallel passages therein opening through opposite ends of said cannula and a first end of said cannula is tapered whereby one of said passages is shorter than the other of said passages.

5. An endotracheal intubation system in accordance with claim 1 wherein said means for coupling said mounting body with said bridge means includes means for moving said mounting body laterally on said bridge means.

6. An endotracheal intubation system comprising:
   a bridge member adapted for pivotal connection over a patient table for performing examinations and operations on a patient on said table;
   an annular gear secured on said bridge member along a central portion of said member;
   a mounting body secured on said bridge member over said gear, said mounting body having a front opening slot shaped to receive said bridge member and said gear in a cylindrical portion of said slot, an indexing finger secured with said mounting body in said slot and a finger operating handle pivotally secured with said mounting body and said finger for moving said finger between gear engaging and release positions for selectively locking said mounting body at a desired angular position on said bridge member, and a handle connected into a top portion of said mounting body for moving said mounting body on said bridge member between said desired angular positions;
   a bracket secured to the bottom of said mounting body;
   a cannula mounting block secured with said bracket for supporting said cannula mounting block from said mounting body over a patient on said table; and
   an endotracheal cannula secured with said mounting block adapted to be suspended in a patient mouth and throat from said mounting block.

7. An endotracheal intubation system in accordance with claim 6 wherein said cannula comprises a first straight end portion and an integral curved central and opposite end portion shaped to pass through the mouth into the throat of a patient, said straight end portion having a flangeless end, said cannula having a plurality of side-by-side parallel passages throughout the length thereof opening through opposite ends for operating and examination tubular apparatus, the end of said cannula along said straight portion having a notch therein whereby one of said passages is shorter than the other of said passages at said end.

8. An endotracheal intubation system in accordance with claim 6 wherein said cannula comprises a straight hollow member having parallel passages throughout the length thereof opening through opposite ends of said member and having one end tapered whereby one of said passages is shorter than the other of said passages at said tapered end.

* * * * *